US010983115B2

(12) United States Patent
Kim et al.

(10) Patent No.: US 10,983,115 B2
(45) Date of Patent: Apr. 20, 2021

(54) REUSABLE OPTICAL FIBER APTASENSOR BASED ON PHOTO-THERMAL EFFECT

(71) Applicant: GWANGJU INSTITUTE OF SCIENCE AND TECHNOLOGY, Gwangju (KR)

(72) Inventors: Min Gon Kim, Gwangju (KR); Bo Bin Lee, Gwangju (KR); Jin Ho Park, Gwangju (KR); Ju Young Byun, Gwangju (KR)

(73) Assignee: GWANGJU INSTITUTE OF SCIENCE AND TECHNOLOGY, Gwangju (KR)

(*) Notice: Subject to any disclaimer, the term of this patent is extended or adjusted under 35 U.S.C. 154(b) by 260 days.

(21) Appl. No.: 15/814,312

(22) Filed: Nov. 15, 2017

(65) Prior Publication Data

US 2018/0136206 A1 May 17, 2018

(30) Foreign Application Priority Data

Nov. 15, 2016 (KR) .................... 10-2016-0152264

(51) Int. Cl.
*G01N 33/543* (2006.01)
*G01N 21/552* (2014.01)
(Continued)

(52) U.S. Cl.
CPC ........ *G01N 33/54366* (2013.01); *B82Y 15/00* (2013.01); *B82Y 20/00* (2013.01);
(Continued)

(58) Field of Classification Search
None
See application file for complete search history.

(56) References Cited

U.S. PATENT DOCUMENTS

| 5,359,681 A | 10/1994 | Jorgenson et al. |
| 7,340,119 B1* | 3/2008 | Xu .................... G01N 21/774 |
| | | 385/12 |

(Continued)

FOREIGN PATENT DOCUMENTS

| JP | 08505475 A | 6/1996 |
| JP | 2001165852 A | 6/2001 |

(Continued)

OTHER PUBLICATIONS

Nano-Aptasensing in Myxcotoxin Analysis: Recent Updates and Progress, Toxins, Oct. 28, 2017, pp. 1-23 (Year: 2017).*

*Primary Examiner* — Neil N Turk
(74) *Attorney, Agent, or Firm* — Loza & Loza, LLP; Heidi L. Eisenhut (57) ABSTRACT

The present invention relates to a reusable optical fiber aptasensor using a photo-thermal effect, and more particularly, to a reusable optical fiber aptasensor using white light and a laser. The aptasensor includes a light emitting unit for selectively emitting one of white light and a laser, a sensor unit including a plurality of aptamers, a plurality of gold nanorods, and a silver mirror, a detector for analyzing a wavelength of inputted light, and an optical fiber for connecting the light emitting unit with the sensor unit, and connecting the detector with the sensor unit, wherein the light emitted from the light emitting unit is totally reflected in the optical fiber and irradiated to the sensor unit, and light reflected from the silver mirror of the sensor unit is irradiated to the detector. Accordingly, the aptasensor easily measures concentration of a target material in a sample using the optical fiber.

6 Claims, 10 Drawing Sheets

(51) Int. Cl.
*G01N 21/77* (2006.01)
*B82Y 20/00* (2011.01)
*B82Y 15/00* (2011.01)
*G01J 3/02* (2006.01)
*G01N 21/78* (2006.01)
*G01N 21/3563* (2014.01)
*G01N 33/53* (2006.01)
*G01N 33/553* (2006.01)
*G01N 33/58* (2006.01)
*G02B 6/122* (2006.01)
*G01N 21/25* (2006.01)
*G01N 33/02* (2006.01)

(52) U.S. Cl.
CPC ............ *G01J 3/02* (2013.01); *G01N 21/3563* (2013.01); *G01N 21/554* (2013.01); *G01N 21/7703* (2013.01); *G01N 21/78* (2013.01); *G01N 33/5308* (2013.01); *G01N 33/54346* (2013.01); *G01N 33/54393* (2013.01); *G01N 33/553* (2013.01); *G01N 33/587* (2013.01); *G01N 33/02* (2013.01); *G01N 2021/258* (2013.01); *G01N 2021/7716* (2013.01); *G01N 2021/7756* (2013.01); *G01N 2021/7773* (2013.01); *G01N 2021/7776* (2013.01); *G01N 2021/786* (2013.01); *G02B 6/1226* (2013.01)

(56) References Cited

U.S. PATENT DOCUMENTS

| | | | | |
|---|---|---|---|---|
| 2007/0025661 | A1* | 2/2007 | Wang | B82Y 15/00 385/37 |
| 2007/0148760 | A1* | 6/2007 | Klesel | G01J 3/0262 435/287.2 |
| 2009/0041404 | A1* | 2/2009 | Stoddart | B82Y 15/00 385/12 |
| 2011/0129846 | A1* | 6/2011 | Huh | B01L 3/5027 435/7.1 |
| 2011/0207237 | A1* | 8/2011 | Sai | G01N 21/554 436/518 |

FOREIGN PATENT DOCUMENTS

| | | |
|---|---|---|
| JP | 2004125748 A | 4/2004 |
| KR | 1020120035749 A | 4/2012 |
| KR | 20130102874 A | 9/2013 |
| WO | 199416312 A1 | 7/1994 |

\* cited by examiner

REUSABLE OPTICAL FIBER APTASENSOR BASED ON PHOTO-THERMAL EFFECT

BACKGROUND OF THE INVENTION

1. Field of the Invention

The present invention relates to a reusable optical fiber aptasensor using a photo-thermal effect, and more particularly, to a reusable optical fiber aptasensor using white light and a laser.

2. Description of the Related Art

With the development of the food industry, dietary patterns have changed, food problems have been rising, and awareness and interest of consumers in food safety have been increasing. Accordingly, a policy to ensure the safety of food ingredients throughout the manufacturing, production, distribution, and final stages is emerging as one of important policies of a nation.

In order to ensure the food safety, it is necessary to manage harmful food factors that are likely to contaminate food. However, the harmful food factors exceeding an allowable standard value are frequently detected in the food despite regulation and management.

The harmful factors of food may be classified into biological, chemical, and physical factors. Biological factors causing great harm to a human body include food poisoning bacteria and virus, and chemical factors causing great harm to the human body include pesticides, heavy metals, fungal toxins, and antibiotics.

To minimize social and economic losses caused by food-borne toxins, it is necessary to ensure the food safety, and sanitary management has to be performed in a reasonable and scientific manner to ensure the food safety. If the entire process from production to consumption of food is not managed sanitarily, the food safety is deteriorated, resulting in food-borne food poisoning. Although ensuring the food safety may not be absolutely perfect, it is necessary to seek the safety as much as possible by eliminating possible harmful factors.

It is necessary to identify the harmful factors that exist in the entire process from production to consumption, and reduce the effects of each factor to an appropriate level that is not detrimental to the human body depending on the possibility and risk of a disease.

An aptasensor is used to identify a toxin contained in the food as described above.

Aptamers have a property of selectively making a strong bond with specific substances, and are widely used as a typical bioreceptor together with antibodies. Unlike antibodies, aptamers form a G-quadruplex structure in a single-strand sequence when being bound to a substance, and may be strongly bound to the substance by a G-rich group. Such a structure may be decomposed again by the high temperature, high salt concentration, etc., and it is possible to freely bind and isolate the aptamer to and from a target material by using the above change in the property of the structure of the aptamer.

However, a regeneration process is necessary to reuse the aptasensor, but the regeneration process is not easy.

SUMMARY OF THE INVENTION

One object of the present invention is to provide an aptasensor capable of easily measuring concentration of a target material in a sample using an optical fiber.

Another object of the present invention is to provide an aptasensor which may be semi-permanently used by topically heating the sensor with a laser to isolate the target material from an aptamer.

According to an aspect of the present invention for achieving the above or other objects, there is provided an aptasensor including a light emitting unit for selectively emitting one of white light and a laser, a sensor unit including a plurality of aptamers, a plurality of gold nanorods, and a silver mirror, a detector for analyzing a wavelength of inputted light, and an optical fiber for connecting the light emitting unit with the sensor unit, and connecting the detector with the sensor unit, wherein the light emitted from the light emitting unit is totally reflected in the optical fiber and irradiated to the sensor unit, and light scattered from the nanorods of the sensor unit is reflected from the silver mirror and irradiated to the detector.

According to one embodiment of the present invention, the aptasensor can easily measure the concentration of the target material in a sample using the optical fiber.

According to another embodiment of the present invention, the aptasensor can be semi-permanently used by topically heating the sensor with the laser to isolate the target material from the aptamer.

DETAILED DESCRIPTION OF THE INVENTION

Hereinafter, embodiments disclosed herein will be described in detail with reference to the accompanying drawings, wherein the same reference numerals are used to designate identical or similar elements, and redundant description thereof will be omitted. The suffixes "module" and "unit" for elements used in the following description are given or used together in consideration of convenience in drafting the specification, and do not have a distinct meaning or role by itself. In addition, in the following description of the embodiments disclosed herein, detailed descriptions of well-known related arts may be omitted when they make the gist of the embodiments rather unclear. In addition, although the accompanying drawings are provided for a further understanding of the embodiments disclosed herein, the technical idea disclosed in the present specification is not limited thereto. It is understood that all modifications, equivalents, and alternative forms can be made without departing from the spirit and scope of the present invention.

Although any of the terms including ordinal numbers such as "first" or "second" may be used herein to describe various elements, the elements should not be limited by the terms. The terms are only used to distinguish one element from another.

When one element is described as being "connected" or "accessed" to another element, it shall be construed as being connected or accessed to the other element directly, but also as possibly having another element in between. Meanwhile, if one element is described as being "directly connected" or "directly accessed" to another element, it shall be construed that there is no other element in between.

Singular forms are intended to include plural forms unless the context clearly indicates otherwise.

In the present specification, the term such as "comprising" or "including" is intended to designate the presence of characteristics, numbers, steps, operations, elements, parts or combinations thereof, and shall not be construed to preclude any possibility of presence or addition of one or more other characteristics, numbers, steps, operations, elements, parts or combinations thereof.

Figure 1:
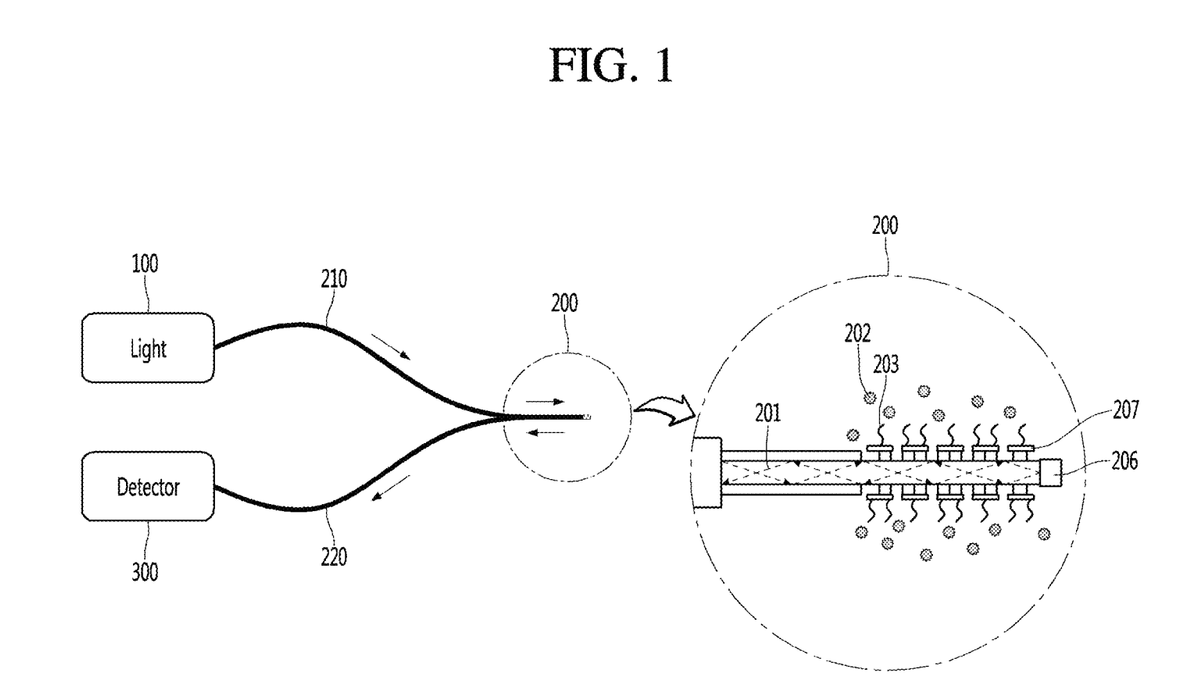
FIG. 1 is a view for describing a concept of a reusable optical fiber aptasensor using a photo-thermal effect according to the present invention.

FIG. 1 is a view for describing a concept of a reusable optical fiber aptasensor using a photo-thermal effect according to the present invention.

Referring to FIG. 1, the reusable optical fiber aptasensor using the photo-thermal effect may include a light output unit 100, a sensor unit 200, a detector 300, and optical fibers 210 and 220.

The light output unit 100 may emit white light or a laser of a specific wavelength.

In one embodiment of the present invention, the light output unit 100 may emit the white light or a laser having a wavelength of 785 nm. In the present invention, the white light may refer to light having a wavelength in all visible light regions. However, wavelengths in infrared and ultraviolet regions may also be included.

In one embodiment of the present invention, the light output unit 100 may emit the laser having the wavelength of 785 nm. However, such a wavelength of 785 nm may be modified into another wavelength, and the laser is not necessarily required to have the wavelength of 785 nm.

In one embodiment of the present invention, the light output unit 100 may selectively emit the white light or the laser having the wavelength of 785 nm. For example, the light output unit 100 may not emit the laser while emitting the white light, and may not emit the white light while emitting the laser having the wavelength of 785 nm.

In one embodiment of the present invention, light emitted from the light output unit 100 is transmitted to the sensor unit 200 through the optical fiber 210.

The optical fibers 210 and 220 have a central portion, that is, a core formed of a material with a high refractive index, and a cladding surrounding the core formed of a material with a low refractive index, so that light passing through the central core may be totally reflected to reach a desired location. The optical fibers 210 and 220 are mainly used for optical communication using light, and may be used as an optical fiber sensor.

In the present invention, the optical fibers 210 and 220 and the sensor unit 200 correspond to application of an optical fiber as a sensor. When an optical fiber is applied as a sensor, the optical fiber may easily transmit light to a place where a measurement target material is located, and interaction is possible between the light and the measurement target material through a medium of glass constituting the optical fiber.

In addition, since the optical fiber may easily transmit desired light to a desired portion, the white light, the laser or the like may be easily transmitted to a desired portion.

Further, types of light being irradiated may be easily changed.

In one embodiment of the present invention, the light emitted from the light output unit 100 and irradiated to the optical fiber 210 may be transmitted to the detector 300 through the optical fiber 220 through the sensor unit 200.

The sensor unit 200 may include an aptamer 203, a gold nanorod (GNR) 207, and a silver mirror 206.

The aptamer 203 is an oligonucleic acid which may be bound to a specific target molecule with high affinity and specificity.

In addition, the aptamer 203 is referred to as a chemical antibody. The aptamer 203 may be easily and stably synthesized, and may be easily changed in structure thereof compared to a single antibody.

Therefore, it is possible to prepare the aptamer 203 which is bound to a toxic substance where an antibody is difficult to be generated, so that the aptamer 203 may be used for high sensitivity measurement of a small molecule, which is difficult to be performed using an antibody.

Figure 2:
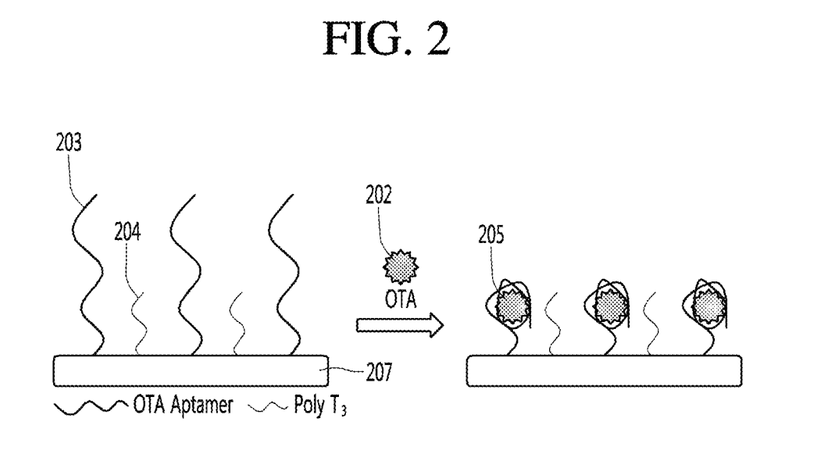
FIG. 2 is a view for describing characteristics of an aptamer according to the present invention.

FIG. 2 is a view for describing characteristics of an aptamer according to the present invention.

Referring to FIG. 2, a binding substance 205 is generated by binding the aptamer 203 to a reactant 202. A short DNA sequence 204 serves to provide a space for the aptamer 203 to properly bind to the reactant 202.

In detail, the aptamer has a property of selectively making a strong bond with a specific substance, and is widely used as a typical bioreceptor together with antibodies. Unlike antibodies, the aptamer forms a G-quadruplex structure in a single-strand sequence when being bound to a substance, and may be strongly bound to the substance by a G-rich group. Such a structure may be decomposed again by the high temperature, high salt concentration, etc., and it is possible to freely bind and isolate the aptamer to and from a target material by using the above change in the property of a structure of the aptamer 203.

Hereinafter, FIG. 1 will be described again.

The gold nanorod 207 may be fixed to a core of an end of the optical fiber from which the cladding is removed using a self-assembly monolayer (SAM) scheme.

In detail, the gold nanorod 207 may be fixed to the end of the optical fiber using a chemical substance having an amine group, a carboxyl group and a thiol group as a functional group.

In addition, the aptamer 203 to which the thiol group is adhered may be attached to the fixed gold nanorod 207.

Therefore, the aptamer 203 may be fixed to the optical fiber.

The silver mirror 206 may be located at an end of the sensor unit.

The silver mirror 206 is prepared by reducing a silver ion, and may reflect light like a mirror.

Due to the silver mirror 206, light emitted from a light source may be absorbed by the gold nanorod, and the remaining light may be absorbed by the detector.

The detailed process thereof will be described below.

The detector 300 is connected to the optical fiber 220, and may measure the light passing through the sensor unit 200.

The detector 300 may measure distribution of wavelengths including a maximum wavelength of an inputted light.

The specific operation of the detector 300 will be described below.

FIGS. 3A to 3D are views for describing an operation of an optical fiber sensor based on a localized surface plasmon resonance (LSPR).

Figure 3A:
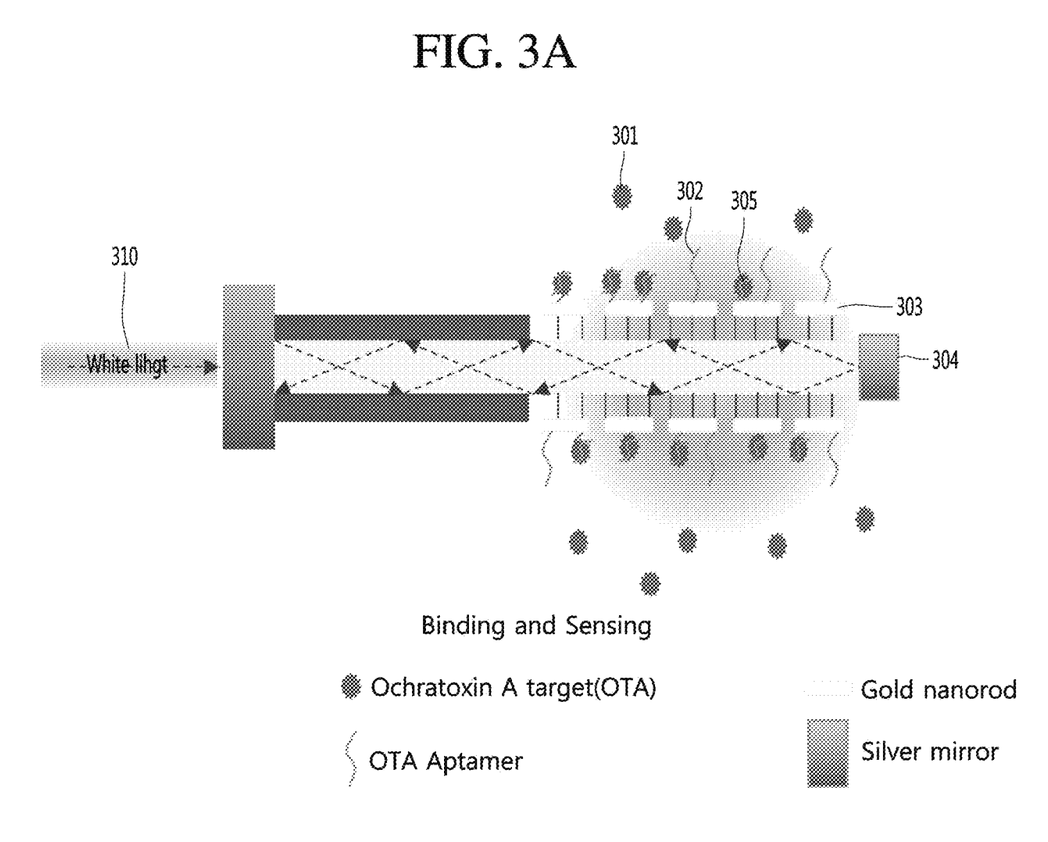
FIGS. 3A to 3D are views for describing an operation of an optical fiber sensor based on a localized surface plasmon resonance (LSPR).

Referring to FIG. 3A, in order to describe the operation of the optical fiber sensor based on the LSPR, it is assumed that the sensor unit 200 is immersed in a measurement target. For example, the sensor unit 200 may be immersed in a liquid to measure concentration of a target contained in the liquid.

When the sensor unit 200 is immersed in the liquid, the aptamer 302 fixed on a surface of the gold nanorod 303 may be bound to a target material 301 to form a binding structure 305.

An LSPR phenomenon on metal nanoparticles is based on a phenomenon that a refractive index of a surface of nanoparticles reacts sensitively. The refractive index of the surface of the gold nanorod 303 increases when the target material 301 is bound to a metal surface to form the binding structure 305. Therefore, a maximum value of an intrinsic absorption wavelength of the gold nanorod 303 is shifted to a long wavelength band (LSPR red shift). In addition, when more target materials 301 are bound to the aptamer 302, more LSPR wavelength shift occurs.

In other words, as the target material 301 is bound to the aptamer 302, an amount of the binding structure 305 increases, and the maximum value of the intrinsic absorption wavelength of the gold nanorod 303 moves more.

Figure 3B:
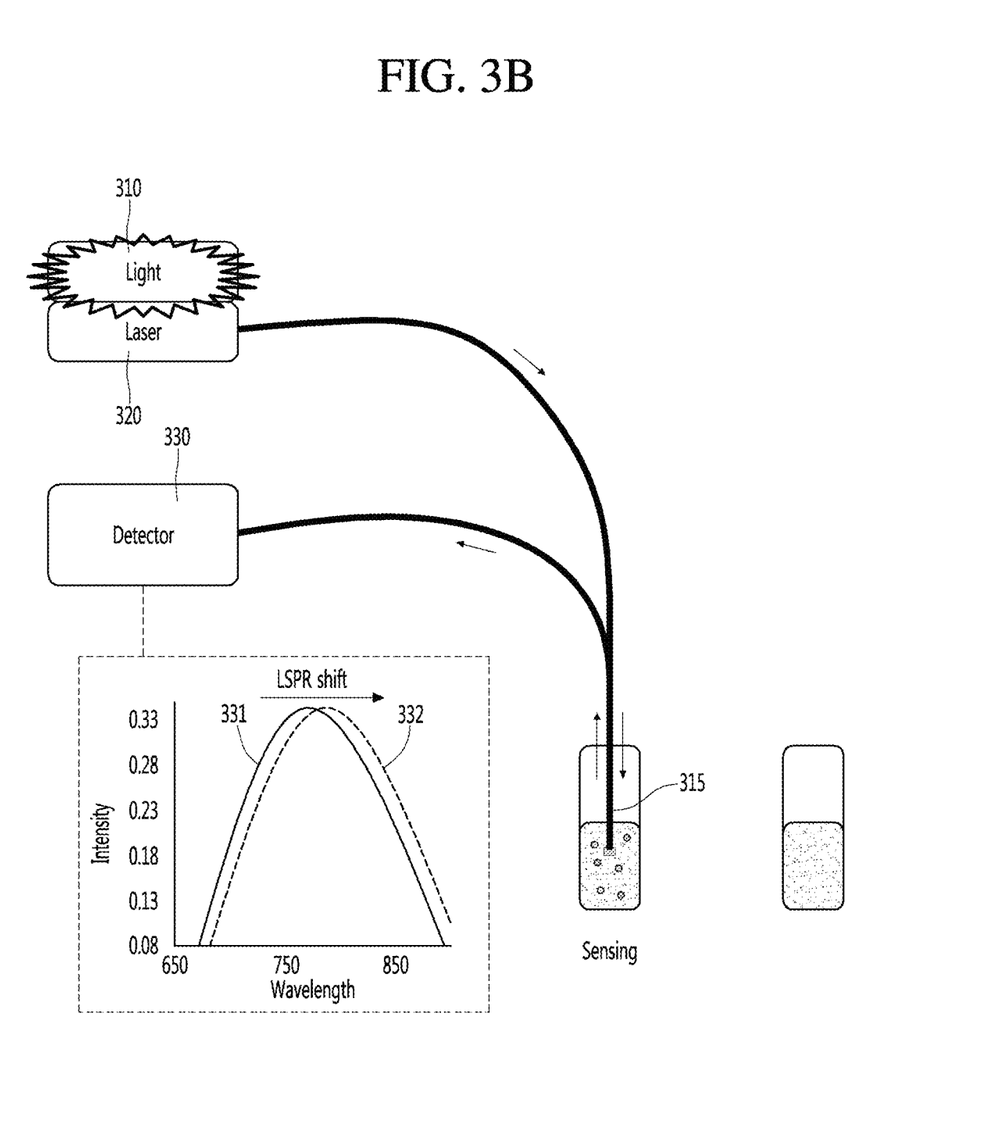

Referring to FIG. 3B, a light emitting unit 100 may selectively transmit light emitted from a white light emitting unit 310 for emitting white light, among the white light emitting unit 310 for emitting the white light and a laser emitting unit 320 for emitting a laser.

The light emitted from the white light emitting unit 310 may pass through the sensor unit 315 immersed in the liquid containing the target material, and may move to the detector 330 by total reflection.

According to a measurement result of the detector, the wavelength distribution is shifted from an initial state 331 to a final state 332 by the LSPR shift.

Figure 3C:
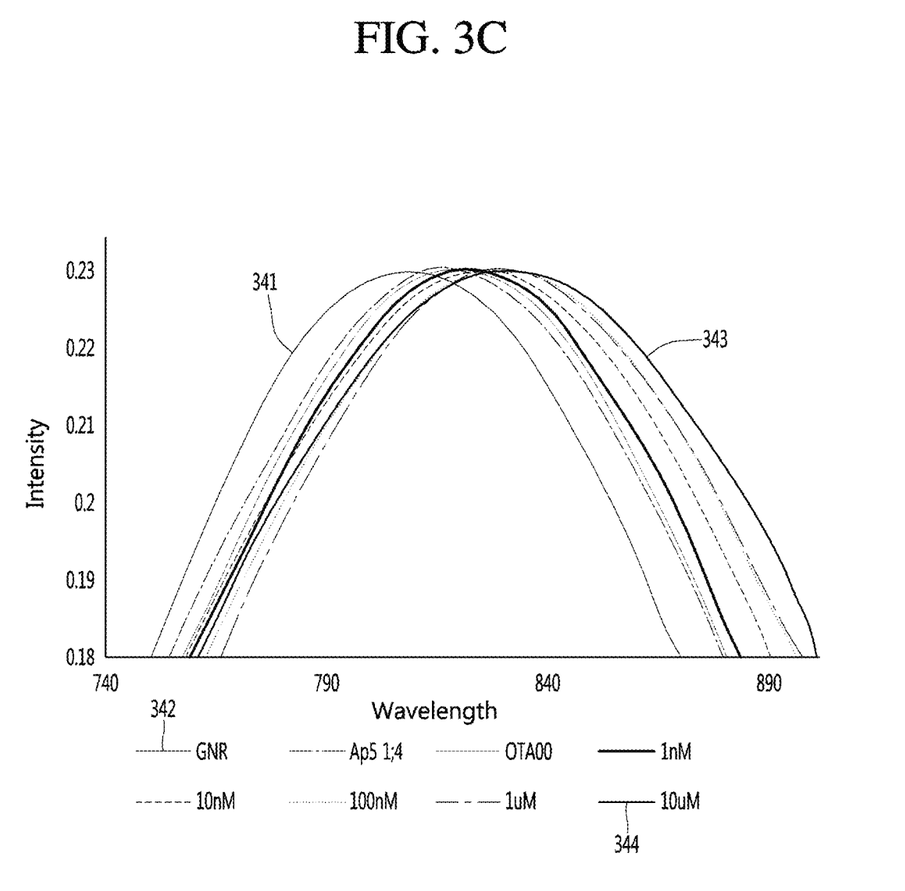

Referring to FIG. 3C, the LSPR shift occurs more depending on the concentration of the target material, which may be observed from a difference between states 341 and 342 where do not contain the target material and states 343 and 344 where the concentration of the target material is 10 μM. In addition, referring to FIG. 3C, the LSPR shift according to the concentration of the target material may be clearly observed.

Figure 3D:
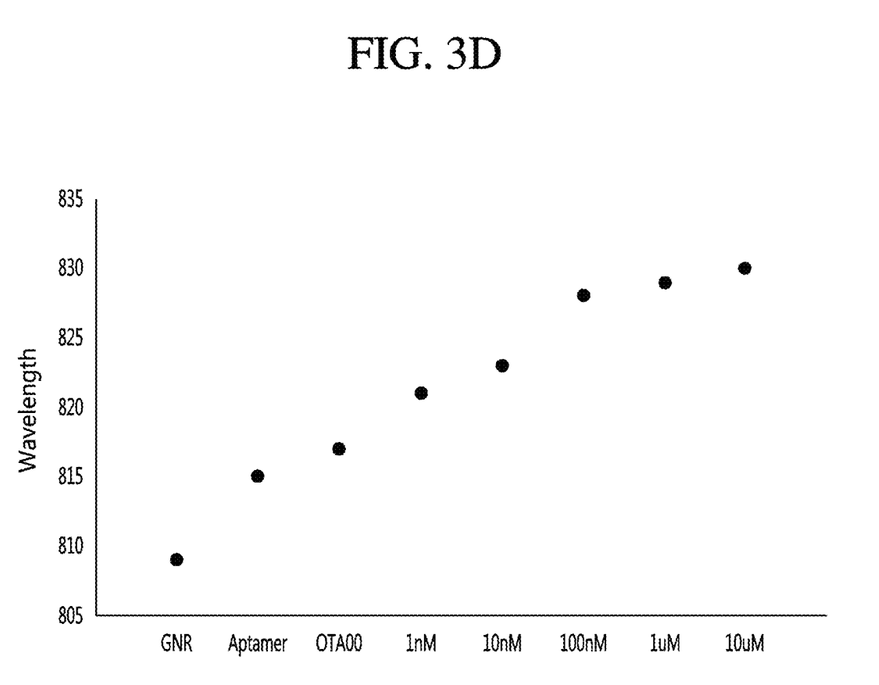

Referring to FIG. 3D, a maximum wavelength of the light measured by the detector changes depending on the concentration of the target material.

In detail, as the concentration of the target material increases, the maximum wavelength of the light measured by the detector increases.

When implementing an LSPR-based sensor on a chip, there is a problem of performing a cumbersome operation of processing a sample on the chip and moving the chip on a spectrometer for measurement. However, according to the present invention, it is possible to perform quantitative measurement by simply immersing the sensor unit connected to the end of the optical fiber into the sample without the cumbersome operation.

FIGS. 4A to 4D are views for describing regeneration of the aptamer using the laser.

Referring to FIGS. 4A to 4D, the light emitting unit 100 may selectively transmit light emitted from a laser emitting unit 420 for emitting a laser, among a white light emitting unit 410 for emitting white light and the laser emitting unit 420 for emitting the laser.

In the sensor unit 425, the gold nanorod may be heated by the laser by absorbing a laser beam.

The light focusing leads to topical temperature rise in the gold nanorod, which allows free binding and isolation of the target material without artificially raising the temperature of a sensor system or additionally providing an excessive amount of salt.

When the gold nanorod is heated, the target material may be isolated from a binding material. When the target material is isolated, the LSPR shift occurs to change the distribution of the wavelength of light from a binding state 434 to an isolation state 433.

When inducing the structural change of the aptamer, if the temperature of the sensor system is increased as in the related art, the sensor may be damaged, or an appropriate target detection environment may be hindered.

Therefore, if the temperature around the aptamer attached to the surface of the nanoparticles is topically raised as in the present invention, damage to the sensor unit may be minimized.

In detail, in the case of an aptamer which reacts with a relatively large material such as a protein or a cell, if the temperature of a sensor is increased, the target material may be destroyed or denatured.

Therefore, it is not suitable for accurate sensing.

In addition, if it is implemented on a chip as in the related art, handling is difficult in a measurement process, so a user is required to be skilled.

However, according to one embodiment of the present invention, when only the gold nanorod is heated using the optical fiber, the laser may be easily irradiated, so that the photo-thermal effect may be easily induced.

Figure 4A:
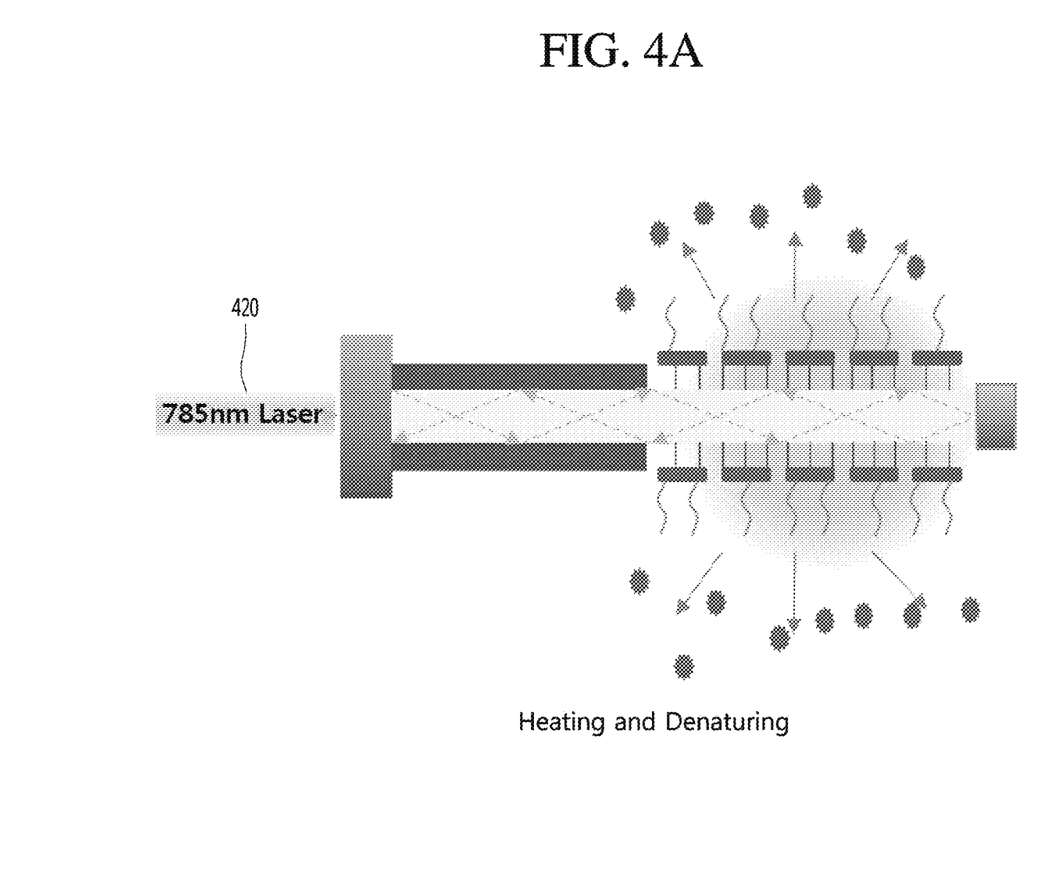
FIGS. 4A to 4D are views for describing denaturation of an aptamer structure using a laser, and regeneration of a sensor.
Figure 4B:
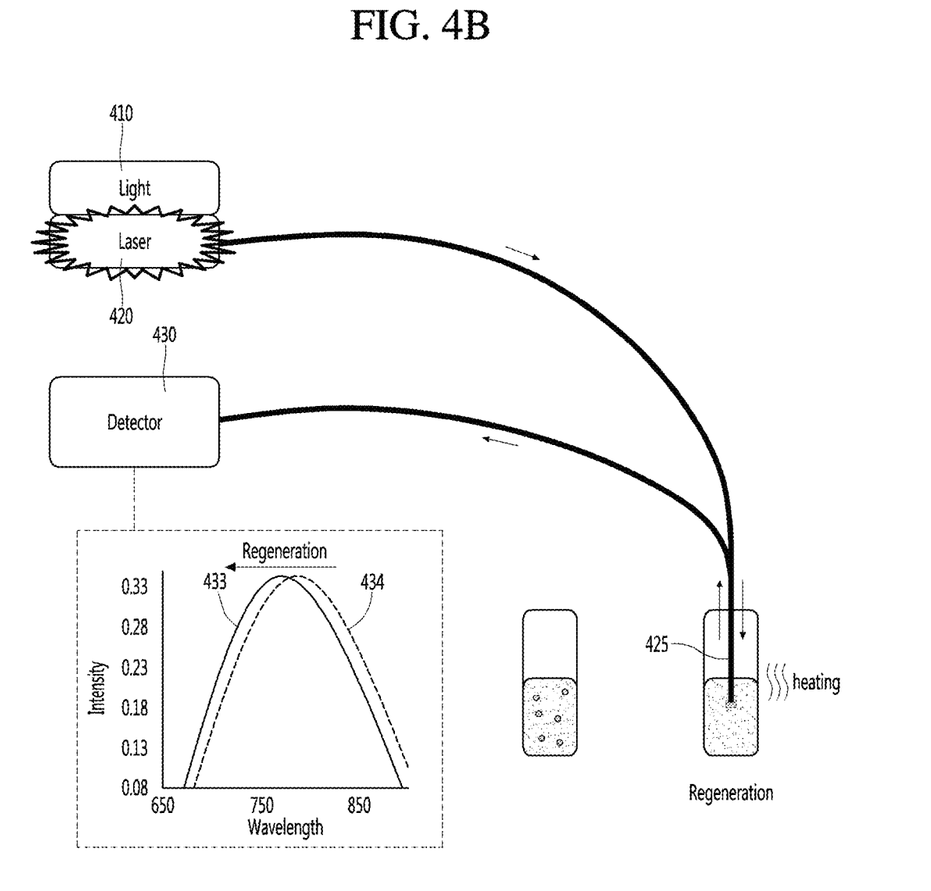
Figure 4C:
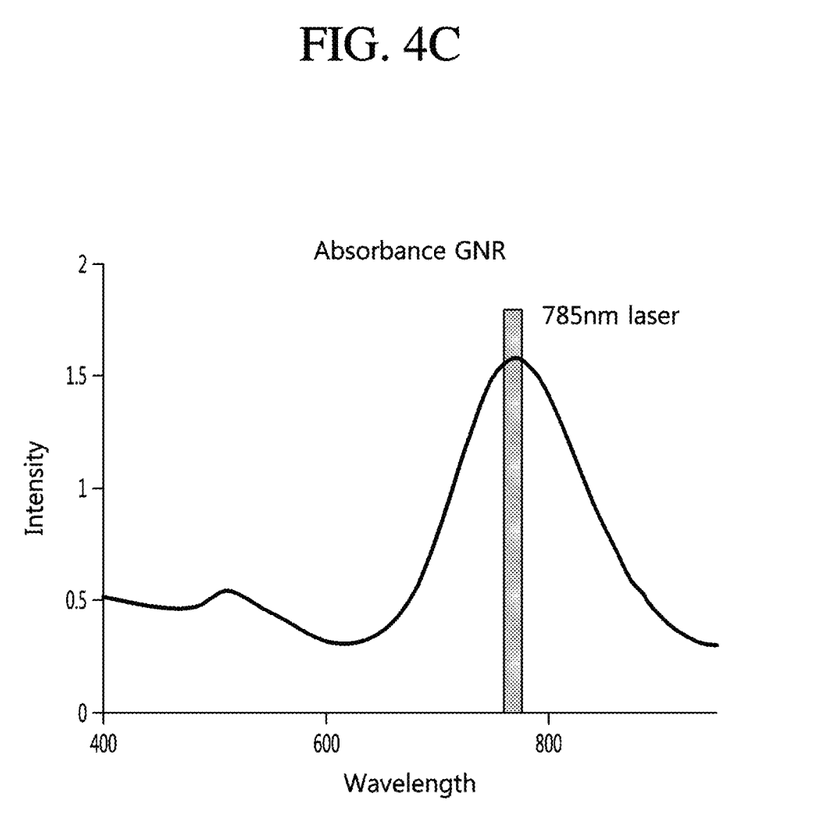

Referring to FIG. 4C, the laser may be focused on the gold nanorod by radiating a laser having a wavelength of 785 nm, which overlaps with the absorption wavelength of the gold nanorod, so that the temperature of the gold nanorod is increased.

Meanwhile, in another embodiment of the present invention, lasers having various wavelengths other than the laser having the wavelength of 785 nm may be used.

However, in order to efficiently increase the temperature of gold nanorod, it is preferable to use the laser having the wavelength of 785 nm.

Therefore, according to the present invention, it is possible to measure the concentration of the target material by using the white light because it is easy to irradiate light due to the characteristics of the optical fiber and easy to alternately irradiate the white light and the laser, and an operation of regenerating the aptamer by using the laser may be easily performed. Regarding the above advantages, it is possible to repeatedly perform a measurement operation by several times with one optical fiber.

Figure 4D:
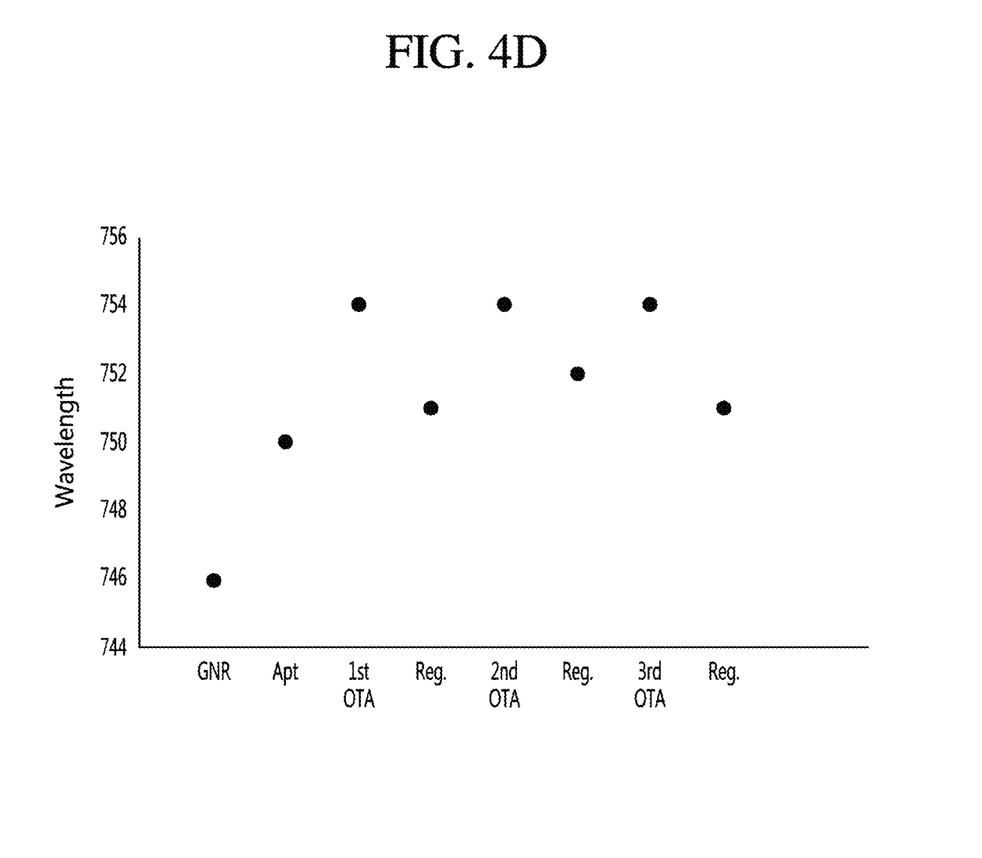

Referring to FIG. 4D, since it is easy to alternately irradiate the white light and the laser, the concentration of the target material may be measured by using the white light, and result values are not significantly different even if the operation of regenerating the aptamer using the laser is performed alternately with the measurement operation.

According to the present invention, the reusable optical fiber aptasensor using the photo-thermal effect may be applied to detection of various materials.

Materials that may specifically react with aptamers may be used to measure a wide variety of harmful chemical substances and biomaterials. In detail, Ochratoxin A (OTA) may be a target material. OTA is one of mycotoxins, is a small molecule with a molecular weight of 403.813 g/mol that mainly contaminates foods such as foods having bread and flour as a main ingredient (nuts such as peanuts and walnuts), coffee, or beer, and is a highly-toxic fungus toxin that damages kidneys. OTA mainly causes a renal cancer, or fatal damage to kidneys and liver.

In addition, according to the present invention, since a simple method of immersing the optical fiber after mixing a collected sample into a solution is used, rapid measurement may be possible in the case of the optical fiber.

The above detailed description should not be construed as limiting in all aspects, but should be considered as being illustrative. The scope of the present invention should be determined by reasonable interpretation of the appended claims, and all modifications within equivalents of the present invention fall within the scope of the present invention.

What is claimed is:

1. An aptasensor comprising:
a light emitting unit including: a white light source for emitting a white light; and a laser for emitting a laser beam, the white light including a light having a wavelength in all visible light and the laser beam having a predetermined single wavelength;
a sensor unit comprising an optical fiber portion from which a cladding is peeled off through a self-assembly monolayer scheme, and including a plurality of gold nanorods fixed to a core of said fiber portion, and including a plurality of aptamers, and a silver mirror, wherein the aptamers are attached to the plurality of gold nanorods, and the silver mirror is disposed adjacent an end of the fiber portion;
a detector for analyzing a distribution of wavelengths of inputted light from the sensor unit; and
an optical fiber connecting the light emitting unit with the sensor unit, and connecting the detector with the sensor unit,
wherein the light emitted from the light emitting unit is totally reflected in the optical fiber and irradiated to the sensor unit, and light reflected from the silver mirror of the sensor unit is irradiated to the detector,
wherein the aptamer is selectively bound to a target material,
wherein the light emitting unit is configured to selectively emit one of the white light for detecting the target material when the white light emitting unit operates and the laser emitting unit does not operate, and the laser beam at the single wavelength suitable to regenerate the aptamer by raising the temperature of the gold nanorods in an amount sufficient to allow free binding and isolation of the target material from the aptamer when the laser emitting unit operates and the white light emitting unit does not operate.

2. The aptasensor of claim 1, wherein the plurality of aptamers are attached to the plurality of gold nanorods via a thiol group.

3. The aptasensor of claim 1, wherein the target material is Ochratoxin A.

4. The aptasensor of claim 1, wherein when the light emitting unit emits the white light, at least one of the aptamers of the sensor unit is bound to the target material to change a refractive index of the gold nanorod, and
the wavelength of light measured by the detector is changed by localized surface plasmon resonance (LSPR) shift.

5. The aptasensor of claim 4, wherein concentration of the target material is measured by the LSPR shift.

6. The aptasensor of claim 1, wherein the laser emits a laser beam having a predetermined single wavelength of 785 nm.

* * * * *